US009526607B2

(12) United States Patent
Seidel et al.

(10) Patent No.: US 9,526,607 B2
(45) Date of Patent: Dec. 27, 2016

(54) CILIARY IMPLANT, CILIARY AUGMENTATION

(71) Applicants: Bethany R. Seidel, Vinemont, AL (US); Steven P. Seidel, Vinemont, AL (US)

(72) Inventors: Bethany R. Seidel, Vinemont, AL (US); Steven P. Seidel, Vinemont, AL (US)

(73) Assignee: Bethany R. Seidel, Vinemont, AL (US)

( * ) Notice: Subject to any disclaimer, the term of this patent is extended or adjusted under 35 U.S.C. 154(b) by 0 days.

(21) Appl. No.: 14/847,196

(22) Filed: Sep. 8, 2015

(65) Prior Publication Data

US 2015/0374489 A1    Dec. 31, 2015

Related U.S. Application Data

(63) Continuation of application No. 14/209,787, filed on Mar. 13, 2014, now abandoned.

(60) Provisional application No. 61/782,408, filed on Mar. 14, 2013.

(51) Int. Cl.
*A61F 2/10*    (2006.01)
*A61B 17/00*    (2006.01)

(52) U.S. Cl.
CPC ........ *A61F 2/10* (2013.01); *A61B 2017/00752* (2013.01); *A61F 2210/0004* (2013.01)

(58) Field of Classification Search
CPC .......................... A61F 2/10; A61B 2017/00752
See application file for complete search history.

(56) References Cited

U.S. PATENT DOCUMENTS

| 6,482,428 | B1 | 11/2002 | Li et al. |
| 7,108,718 | B1 | 9/2006 | Li et al. |
| 7,758,641 | B2 | 7/2010 | Tse |
| 2009/0198335 | A1 | 8/2009 | Barbosa |
| 2009/0254071 | A1 | 10/2009 | Williamson et al. |
| 2010/0211186 | A1 | 8/2010 | Senders et al. |
| 2011/0144750 | A1 | 6/2011 | Knize et al. |

*Primary Examiner* — Thomas J Sweet
*Assistant Examiner* — Daniel Bissing
(74) *Attorney, Agent, or Firm* — James P. Hanrath; Much Shelist

(57) ABSTRACT

A prosthesis for eyelash replacement, restoration, or augmentation includes an implantable base serving a substrate at a ciliary implant site in proximity to a native eyelash line, and a plurality of artificial eyelash hairs secured to the implantable base at intervals along and extending from the implantable base to mimic the look of real human eyelashes. The implantable base may be composed of an absorbable material or a non-reactive, non-absorbable substance and may be curvilinear, rectangular, or round with an annular cross-section in shape. The plurality of artificial eyelash hairs are of a flexible material, preferably composed of a keratin-base or inert fiber, secured, knotted, permanently fixed to the implantable base to mimic native eyelash. A method of eyelash replacement, restoration, or augmentation comprises selecting a ciliary implant site in proximity to a native eyelash line, making an incision corresponding to the ciliary implant site deepened to a plane beneath the orbicularis muscle, and implanting at the ciliary implant site an orientated prosthesis implant base having, or adapted to securely receive, a plurality of artificial eyelash hairs, the prosthesis being oriented to replace, restore, or augment eyelashes. The incision is then closed.

15 Claims, 2 Drawing Sheets

CILIARY IMPLANT, CILIARY AUGMENTATION

CROSS-REFERENCE TO RELATED APPLICATIONS

This patent application is a Continuation Application of and claims the benefit of U.S. patent application Ser. No. 14/209,787 entitled "CILIARY IMPLANT, CILIARY AUGMENTATION" filed Mar. 13, 2014 which claims the benefit of U.S. Provisional Patent Application 61/782,408 entitled "CILIARY IMPLANT, CILIARY AUGMENTATION" filed Mar. 14, 2013, both of which are incorporated herein by reference in their entirety.

FIELD OF THE INVENTION

The present invention relates to ciliary eyelash augmentation and more particularly to a replacement, augmentation, or restoration of the eyelashes with a prosthesis.

BACKGROUND OF THE INVENTION

Women have long sought methods of eyelash enhancement. In many cultures, women desire thick and long eyelashes. Historically, mascara, faux eyelashes and most recently, Latisse® have been used to obtain these objectives. However, each of these methods has drawbacks. Mascara requires frequent re-application, is messy and only moderately successful. Faux eyelashes are difficult to apply, require an adhesive for fixation, expensive and onetime use. Latisse® requires ongoing application and is very expensive. Additionally, side effects have been described such as allergic reaction, skin hyperpigmentation, pruritis and iris darkening. Even though these methods have gained considerable popularity and commercial success, there has been a continuing need for improvement.

A search report produced the following U.S. Patents under the category of "Eyelid implant" and "Scleral prostheses". Ciliary implant would generally fall under the same category.

| | | | |
|---|---|---|---|
| 1 | US20090254071A1 | System and method for identifying a position to insert a scleral prosthesis into an eye | Oct. 8, 2009 |
| 2 | US20100211186A1 | Electroactive polymer actuation of implants | Aug. 19, 2010 |
| 3 | US20090198335A1 | Infra-orbital implant | Aug. 6, 2009 |
| 4 | US20110144750A1 | Brow lift implant and method | Jun. 16, 2011 |
| 5 | U.S. Pat. No. 6,482,428 B1 | Weighted eyelid implant | Nov. 19, 2002 |
| 6 | U.S. Pat. No. 7,108,718 B1 | Gold eyelid weight implant | Sep. 19, 2006 |
| 7 | U.S. Pat. No. 7,758,641 B2 | Extraocular muscle prosthesis | Jul. 20, 2010 |

While the patents referenced above are instructive of varying eyelid implants and prostheses for a patient's eye, the particular implants thereof primarily address other concerns distinct and unrelated to the function, description and/or purpose of the present Ciliary Implant, Ciliary Augmentation disclosure which describes replacement, augmentation, or restoration of the eyelashes with a prosthesis.

SUMMARY OF THE INVENTION

In accordance with an aspect of the present invention there is provided a prosthesis for eyelash replacement, restoration, or augmentation comprising an implantable base serving a substrate at a ciliary implant site in proximity to a native eyelash line, and a plurality of artificial eyelash hairs secured to the implantable base at intervals along the implantable base and extending from the base. The implantable base may be composed of an absorbable material or a non-reactive, non-absorbable substance and may be curvilinear, rectangular, or round with an annular cross-section in shape. The plurality of artificial eyelash hairs are of a flexible material, preferably composed of a keratin-base or inert fiber, secured, knotted, permanently fixed to the implantable base to mimic native eyelash.

In accordance with an aspect of the present invention there is provided a method of eyelash replacement, restoration, or augmentation comprising selecting a ciliary implant site in proximity to a native eyelash line, making an incision corresponding to the ciliary implant site deepened to a plane beneath the orbicularis muscle, and implanting at the ciliary implant site an orientated prosthesis implant base having, or adapted to securely receive, a plurality of artificial eyelash hairs, the prosthesis being oriented to replace, restore, or augment eyelashes. The incision is then closed.

Numerous other advantages and features of the invention will become readily apparent from the following detailed description of the invention and the embodiments thereof, from the claims, and from the accompanying drawings.

BRIEF DESCRIPTION OF THE DRAWINGS

Embodiments of the present invention will now be described, by way of example only, with reference to the attached Figures, wherein.

DETAILED DESCRIPTION OF THE EMBODIMENTS

Figure 1:
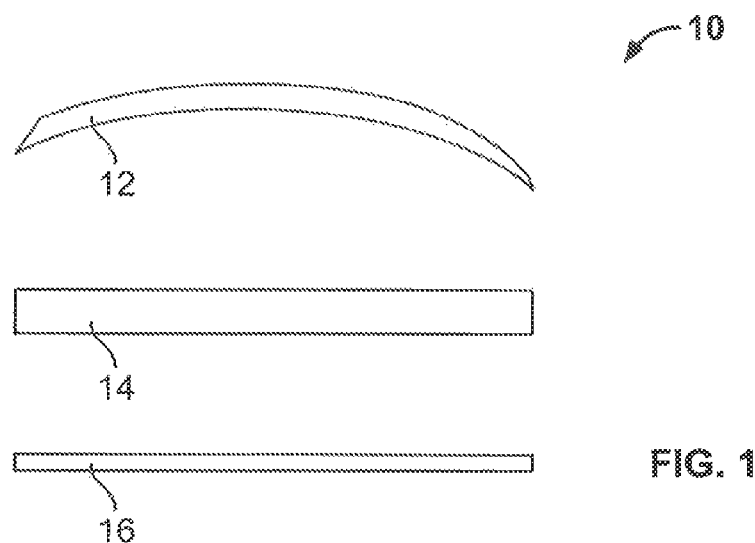
FIG. 1 depicts a frontal view of three different shapes of a prosthesis implant base having, or adapted to securely receive, a plurality of artificial eyelash hairs according to an embodiment of the invention.

While the invention is susceptible to embodiments in many different forms, there are shown in the drawings and will be described herein, in detail, the preferred embodiments of the present invention. It should be understood, however, that the present disclosure is to be considered an exemplification of the principles of the invention and is not intended to limit the spirit or scope of the invention and/or claims of the embodiments illustrated.

Ciliary Implant or Augmentation in accordance with embodiments of the invention is a novel surgical procedure involving the use of an orientated prosthesis implant base having, or adapted to securely receive, a plurality of artificial eyelash hairs to restore or enhance upper or lower lid eyelashes and for correcting eyelash loss due to chemotherapy, certain disease processes or for cosmetic purposes.

Indications:

Ciliary implant or Augmentation is indicated for patients with eyelash loss due to chemotherapy, madarosis (total eyelash loss due to other medical conditions) and patients desiring thicker, longer lashes.

Procedure:

A supraciliary incision is made just above and parallel to the native lash line. The incision is deepened to a plane beneath the orbicularis muscle. Meticulous hemostasis is obtained. A previously selected implant prosthesis (see description below) is placed in this incision and properly oriented. A medical grade tissue adhesive is used to close the incision. Three interrupted 7-0 nylon sutures are placed to complete the closure.

Implant Descriptions and Overview:

The implant base can be composed of either a non-reactive, non-absorbable substance or an absorbable material such as is used in many surgical sutures. The implant base can be of varying lengths depending on patients' needs and desires, such as about 2, 2.5, or 3 cm in length. In FIG. 1 three implant bases 10 are illustrated, one being curvilinear 12, one being strip-like rectangular 14, and one being round having an annular cross-section 16.

The implant base is an extremely thin, curvilinear, rectangular, or round silastic or soft pliable plastic strip which is slightly shorter in length than the patient's natural eyelash line, such as 2, 2.5, or 3 cm in length, but can be shortened as needed. The implant base may consists of an extremely thin absorbable material as is found in certain surgical sutures such as polyglactin or polydioxanone or the brands PDS and vicryl/polysorb.

Figure 2:
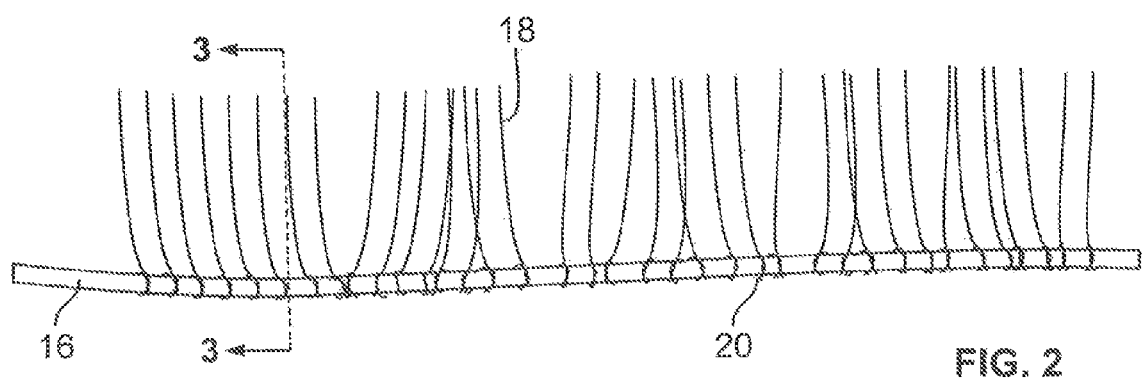
FIG. 2 depicts a frontal view of the annular cross-section implant base of FIG. 1 with a plurality of artificial eyelash hairs secured by knot thereto.
Figure 3:
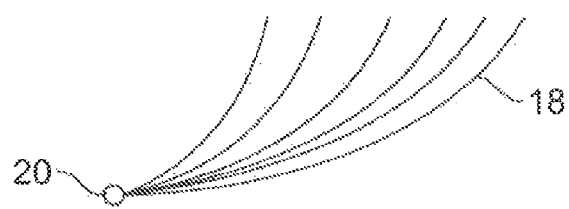
FIG. 3 depicts a cross section side view of the implant base with knotted artificial eyelash hairs of FIG. 2 taken along line 3-3 of FIG. 2.

Referring now to FIGS. 2 and 3, attached to the annular cross-section implant base 16 depicted therein at intervals are a plurality of artificial eyelash hairs 18 composed of a keratin-base or other inert fiber that mimics human lashes, the hairs being about 1 to 1.2 cm in length or as shortened or trimmed as desirable. The artificial eyelash hairs can vary in length, thickness, spacing and color again meeting the patients' needs and desires. Each individual artificial eyelash hair has a small knot 20 at its base with the implant base 16 which serves as an anchor to keep the lash in position once the suture material is absorbed. Individual artificial hairs or lashes are knotted to the implant base 16, either before incision/implantation or post-incision during implantation.

The length of the implant base 10 can be customized for either the absorbable or non-absorbable base. This would be necessary in case of segmental eyelash loss or to meet certain cosmetic requests; i.e. some women find full lateral eyelashes to be cosmetically appealing.

Figure 4:
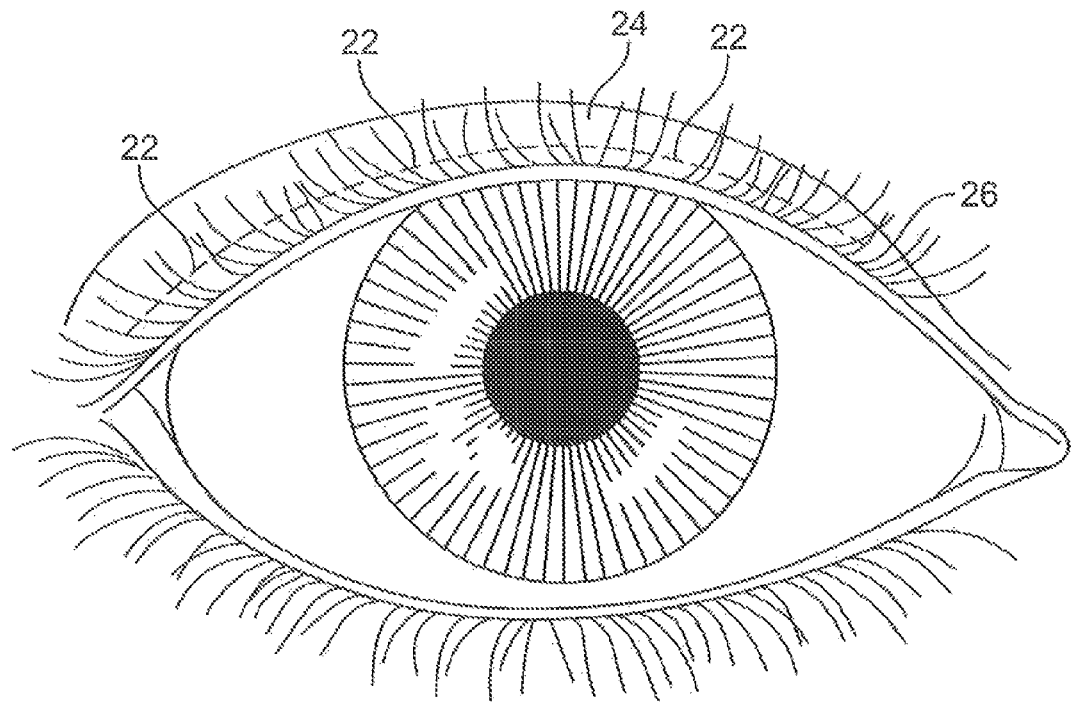
FIG. 4 depicts an incision line to an eyelid which defines a ciliary implant site according to an embodiment of the invention, the eyelid being in an open position.
Figure 5:
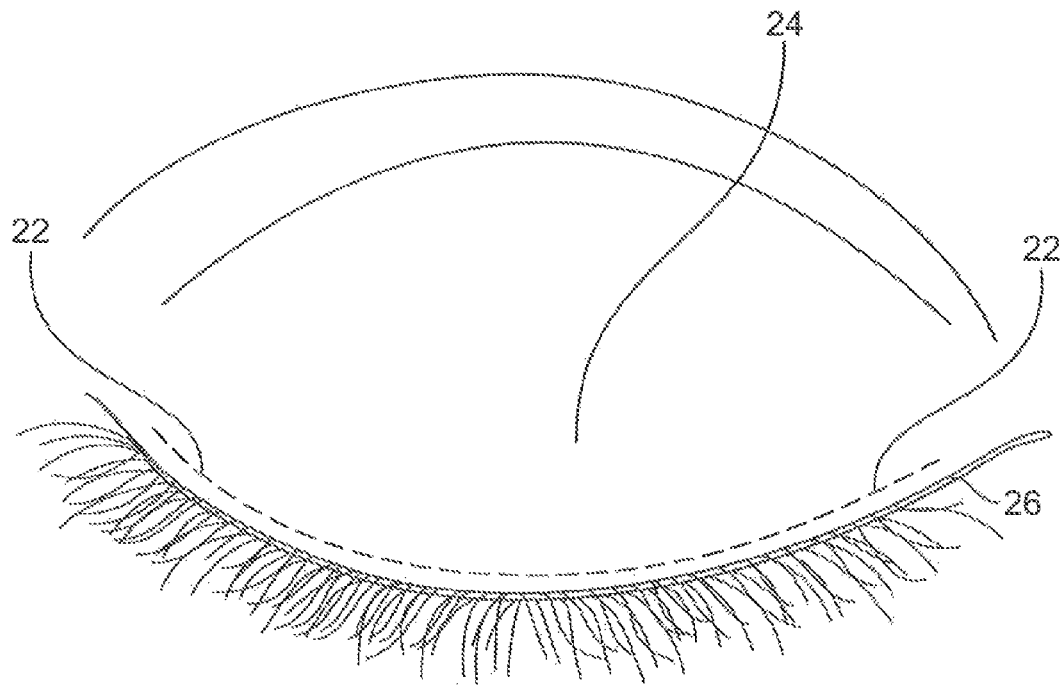
FIG. 5 depicts an incision line to an eyelid which defines a ciliary implant site, the eye lid being in a closed position.

At FIGS. 4 and 5 there is illustrated a supraciliary incision line 22 to an upper eyelid 24 which is made just above and parallel to the native lash line 26. The incision line 22 defines a ciliary implant site 28. FIG. 4 illustrates the same with the upper eye lid in an open position and FIG. 5 with the upper eye lid in a closed position.

Recovery:

The procedure is done under sedation or local anesthesia on an outpatient basis. Patients are asked to refrain from strenuous activity for one week post-procedure. They are asked to sleep in an elevated position and apply cold compresses for the first week to minimize swelling. They may shower on post-operative day one. No specific care is required for the incision. Patient must wear sunglasses when outside due to light sensitivity. Sutures are removed one week post-procedure. Assuming no complications have occurred, the patient may resume regular activity after suture removal.

From the foregoing and as mentioned above, it will be observed that numerous variations and modifications may be effected without departing front the spirit and scope of the novel concept of the invention. It is to be understood that no limitation with respect to the specific methods and device illustrated herein is intended or should be inferred. It is, of course, intended to cover by the appended claims all such modifications that fall within the scope of the claims.

We claim:

1. A method of eyelash replacement, restoration, or augmentation comprising:
   selecting a ciliary implant site in proximity to a native eyelash line,
   making an incision corresponding to the ciliary implant site deepened to a plane beneath the orbicularis muscle, and
   implanting at the ciliary implant site an orientated prosthesis implant base having, or adapted to securely receive, a plurality of artificial eyelash hairs, the prosthesis being oriented to replace, restore, or augment eyelashes.

2. The method of claim 1 further comprising closing the incision.

3. The method of claim 1 wherein said prosthesis implant base is composed of an absorbable material.

4. The method of claim 1 wherein said prosthesis implant base is composed of a non-reactive, non-absorbable substance.

5. The method of claim 1 wherein said prosthesis implant base is about 2, 2.5, or 3 cm in length.

6. The method of claim 1 wherein said prosthesis implant base is curvilinear.

7. The method of claim 1 wherein said prosthesis implant base is rectangular.

8. The method of claim 1 wherein said prosthesis implant base has an annular cross-section.

9. The method of claim 1 wherein said prosthesis implant base is silacone elastomer.

10. The method of claim 1 wherein said prosthesis implant base a pliable silacone elastomer strip.

11. The method of claim 1 wherein said prosthesis implant base is shorter in length than the native eyelash line.

12. The method of claim 1 wherein said plurality of artificial eyelash hairs are of a flexible material.

13. The method of claim 1 wherein said plurality of artificial eyelash hairs are a keratin-base or inert fiber.

14. The method of claim 1 wherein said plurality of artificial eyelash hairs are fixed permanently to said prosthesis implant base.

15. The method of claim 1 wherein said plurality of artificial eyelash hairs are about 1 to 1.2 cm in length.

* * * * *